United States Patent
Wadman

(10) Patent No.: US 8,422,007 B2
(45) Date of Patent: Apr. 16, 2013

(54) OPTICAL MEASUREMENT DEVICE WITH REDUCED CONTACT AREA

(75) Inventor: Sipke Wadman, Waalre (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 885 days.

(21) Appl. No.: 12/158,497

(22) PCT Filed: Dec. 18, 2006

(86) PCT No.: PCT/IB2006/054925
§ 371 (c)(1),
(2), (4) Date: Jun. 20, 2008

(87) PCT Pub. No.: WO2007/072403
PCT Pub. Date: Jun. 28, 2007

(65) Prior Publication Data
US 2009/0002718 A1 Jan. 1, 2009

(30) Foreign Application Priority Data
Dec. 23, 2005 (EP) ..................... 05112941

(51) Int. Cl.
G06K 9/74 (2006.01)
G01N 21/57 (2006.01)

(52) U.S. Cl.
USPC ........ 356/237.1; 356/71; 356/445; 250/201.1

(58) Field of Classification Search .................. 356/612, 356/71, 237.1
See application file for complete search history.

(56) References Cited

U.S. PATENT DOCUMENTS

| | | | |
|---|---|---|---|
| 4,846,184 A | 7/1989 | Comment et al. | |
| 5,241,369 A * | 8/1993 | McNeil et al. | 356/445 |
| 5,541,413 A * | 7/1996 | Pearson et al. | 250/339.11 |
| 5,637,873 A * | 6/1997 | Davis et al. | 250/339.11 |
| 5,672,875 A * | 9/1997 | Block et al. | 250/343 |
| 5,912,741 A * | 6/1999 | Carter et al. | 356/445 |
| 6,429,927 B1 * | 8/2002 | Borza | 356/71 |
| 6,577,397 B1 | 6/2003 | Wadman | |

(Continued)

FOREIGN PATENT DOCUMENTS

| | | |
|---|---|---|
| EP | 0516457 A2 | 12/1992 |
| EP | 1488737 A1 | 12/2004 |

(Continued)

OTHER PUBLICATIONS

M. E. Becker; "Evaluation and Characterization of Display Reflectance", Displays, Elsevier Science Publ. BV., Barking, GB, vol. 19, No. 1, Jun. 2, 1998, pp. 35-54, XP004134069.

(Continued)

*Primary Examiner* — Gregory J Toatley
*Assistant Examiner* — Rebecca C Bryant

(57) ABSTRACT

An optical measurement device for measuring an optical appearance of a surface of a sample includes a measuring head which can be brought into contact with the surface of the sample. The measuring head includes an illumination device for illuminating the surface with an illumination beam, and a detection device or detecting a response beam. The response beam is the response of the sample to the illumination beam. The detection device includes a screen for intercepting the response beam, where the screen extends approximately a quarter hemisphere in order to realize measuring head with a small contact area with the surface.

18 Claims, 3 Drawing Sheets

U.S. PATENT DOCUMENTS

| | | | |
|---|---|---|---|
| 6,870,620 B2 | 3/2005 | Faupel et al. | |
| 7,050,158 B2 * | 5/2006 | Ma et al. | 356/71 |
| 7,119,903 B1 | 10/2006 | Jones | |
| 7,123,361 B1 * | 10/2006 | Doughty | 356/316 |
| 2002/0080357 A1 * | 6/2002 | Dana | 356/445 |
| 2003/0050543 A1 | 3/2003 | Hartmann | |

FOREIGN PATENT DOCUMENTS

| | | |
|---|---|---|
| WO | 0037923 | 6/2000 |
| WO | 0135077 A1 | 5/2001 |
| WO | 0139665 A2 | 6/2001 |
| WO | 02057726 A2 | 7/2002 |
| WO | 03079881 A2 | 10/2003 |
| WO | 2004077032 A1 | 9/2004 |
| WO | 2004077033 A1 | 9/2004 |

OTHER PUBLICATIONS

M. Mehrubeoglu et al; "Characterization of Skin Lesion Texture in Diffuse Reflectance Spectroscopic Images", Proc. 4th IEEE Southwest Symposium on Image Analysis and Interpretation Apr. 2-4, 2000, Austin, TX, USA pp. 146-150, XP002432386.

Q. Qingjun et al; "Evaluation of Contact Status Between Probe and Skin for Mnoninvasive Blood Sensing With NIR Reflectance Spectroscopy", ALT'03 Intl. Conf. on Advanced Laser Tech.: Biomedical Optics Sep. 19-23, 2003, Silsoe, UK, vol. 5486, No. 1, pp. 28-34, XP002432387.

* cited by examiner

OPTICAL MEASUREMENT DEVICE WITH REDUCED CONTACT AREA

The invention relates to an optical measurement device for measuring an optical appearance of a surface of a sample, in particular of the surface of a human skin, comprising a measuring head which can be brought into contact with the surface of the sample, wherein the measuring head comprises an illumination device for illuminating the surface with an illumination beam, a detection device for detecting a response beam, wherein the response beam is a response of the illumination of the sample with the illumination beam.

An object, in particular a surface of the object, called "sample" in the following, shows an optical appearance. The optical appearance of the surface of the sample is a result of what the surface does with light from the environment, in particular is the optical appearance determined by a sum of an overall response of the surface to the light, called illumination beam in the following, incident on the surface.

The optical appearance can be shiny and glossy or dull, rough or smooth, with a texture of a preferred direction or randomly textured. The optical appearance may be of a consistent color or comprises color flops; the optical appearance may be opaque or translucent or show a reflectivity like a mirror.

An illumination beam incident on the surface of the sample is, depending on the macroscopic properties of the surface, like roughness and texture and the materials properties—reflected, scattered, absorbed, or changed in color. The direction of texture, for instance, is visible due to the scattering of the illumination beam. As an example, a flat, shiny surface reflects a higher percentage of the incident radiation beam as a surface of a dull sample.

Different methods for an assessment of the optical appearance are known, which are applied depending on the material of the sample and the properties of the surface as well as the size and nature of the sample having the surface.

In general, visual measurements are made by visually comparing the surface of the sample to a certain standard surface by trained personnel. Visual measurement devices, like a gloss-meter or a color-meter for the measurement of the gloss or the color, as well as a mechanical micro geometrical measurement device like a profilo-meter for the determination of the roughness of the surface, are known.

A gloss-meter is a simple device that projects an illumination beam onto a surface and measures the intensity ratio of the reflected illumination beam and the diffused radiation in a halo around the specula reflection. This is done under a fixed angle of incidence.

In a mechanical micro geometrical measurement device, using a contact probe, a one-dimensional, two-dimensional or three-dimensional map of the surface is generated, resulting in a quantity to be measured, called roughness. A correlation between the measured roughness of the surface and the optical appearance of the surface is then generally performed.

More sophisticated optical measurement devices for inspecting the surface of a sample in order to obtain the assessment to the optical appearance are known as photogoniometers and scatterometers.

In a scatterometer a collimated radiation beam is directed onto the surface to be inspected and detected in a spatial and angular resolved way, resulting in a two-dimensional image.

A photogoniometer uses digital image capture and the projection of the emerging light on a diffusing screen. The quantity, measured is called bi-directional transmission or reflection distribution function, abbreviated BTDF or BRDF. This function is defined as a quotient of the luminescence of a surface element in a given direction by the luminescence incident on the surface, and hence expresses the emerging light distribution for a given incident direction.

An optical measurement device, which belongs to the class of scatterometers, called Parousiameter, is known from the U.S. Pat. No. 6,577,397. The optical measurement device comprises a radiation source emitting a radiation beam and a device for collimating the radiation beam, such that a collimated radiation beam is incident on the surface of the sample to be investigated. A response beam scattered from the surface of the sample is detected by a hemispherical screen. The screen is imaged in a digital camera using a wide-angle optics. The captured image is transformed to a computer for analyses and an extraction of the relevant data. The sample to be investigated is mounted on a so-called stage, wherein the stage is adjustable in order to allow changes in the azimuth of the sample.

The hemispherical screen, called dome, has a base plate with a control hole through it, through which a part from the sample is visible. Due to the extension of the base plate and the geometry thereof, only flat samples are inspecting able. These samples are positioned below the control hole. This is to guarantee a reversible and tight connection of the base plate of Parousiameter to the sample to be inspected during the whole measurement. In the device discussed above, it is important not to change the position of the sample relative to the control hole in the base plate in order to direct the radiation beam on the sample area over the surface during the complete measurement.

Therefore, the Parousiameter discussed above is not suitable for the inspecting of small surface areas of larger objects and samples and for the inspection of non-planar surfaces.

An apparatus for the inspection of a non-planar surface is known from the U.S. Pat. No. 6,870,620 B2. The apparatus comprises a probe head, wherein the probe head is configured to conform to a non-uniform and/or non-planar surface area and comprises an interrogation surface that is intended to be positioned adjacent or pushed into contact with the surface. During the measurement process, the interrogation surface is pressed into contact with the non-uniform surface to cause individual ones of the interrogation devices to move, thereby causing the probe head to conform to the non-uniform surface.

This allows the measurement of a non-planar surface, which has only a small variation from being planar. There is a need for the inspection of a curved surface, in particular of a concave curved surface and for the inspection of a surface area of a larger object.

Therefore, it is the object of the present invention to provide an optical measurement device, which allows the inspection of a curved, in particular a concave curved surface.

The object is solved according to the invention by an optical measurement device as mentioned at the outset, in that the detection device comprises a screen, wherein the screen is extending approximately a quarter hemisphere in order to realize the measuring head with a small contact area with the surface.

A screen extending approximately a quarter hemisphere occupies only a small space in the measuring head of the optical measurement device. Therefore, the measuring head can be designed such that it is suitable to scan a curved surface. This space is preferably used to position an illumination component of the illumination device at a close range to the surface.

The position of the screen, which covers a smaller area than the standardly used, full hemispherical screen is optimized in order to have a high sensitivity and image a high percentage of the reflected and/or scattered radiation beam.

The screen is preferably centered on the nominal reflection angle. With that space is gained and the close position of the illumination component to a position, where the illumination beam is hitting the surface, can be realized. Therefore, the measuring head can have a small size.

The small size of the measuring head in contact with the surface allow the positioning of the measuring head in curved, in particular in concave curved surfaces.

The optical measurement device is used in particular to inspect the surface of the skin of a human being and estimate the optical appearance of the skin. A particular area with a concave curved surface is the inside of a hand.

Because of the small size of the screen and small the size of the measuring head, the measuring head can be used in a mobile optical measurement device, which allows the inspection of certain surface areas of larger objects.

The two-dimensional image formed on the screen represents the angular distribution of the illumination beam reflected and/or scattered at the surface of the sample.

In a preferred embodiment of the invention, the screen is a substantially flat screen.

An optimized screen is made flat in order to avoid secondary intensities. A flat screen allows to position the screen in a defined position to the surface of the sample.

An idle position of the screen with respect to the surface of the sample is different from being parallel to the surface and/or being perpendicular to the surface.

In a further preferred embodiment of the invention, the detection device comprises an image detection component in order to image the screen.

The image detection component is capturing the two-dimensional image of the screen. This is necessary, because the distribution pattern visualized on the screen represents only a momentary image. In order to perform further processing of the distribution pattern and compare different distribution patterns, the image has to be imaged and stored in a long-term way. This is performed by the image detection component comprising a radiation sensitive component and imaging the distribution pattern by this. Preferably the image is digitalized and the information given by the distribution pattern can be processed further in a computer.

The image is a Fourier-like transform of the physical properties of the surface of the sample, in which physical properties of the surface of the sample are transformed to an angular variation of the response beam. The use of the image detector component, allows in particular a fast capture of the image.

In a further preferred embodiment of the invention, the image detection component is a camera, in particular a digital camera.

A camera is an easy and cheap way to store an image from the screen in a long-term way. The camera is preferably a digital camera that is capable of acquiring a rapid succession of images to resolve rapid changes in time. The information is visualized, transferred into electric signals and transferred into an electronic data file, which can be stored on an electronic storage medium like a CD or a DVD and the like.

In a further preferred embodiment, the illumination device comprises a radiation source emitting a radiation beam from which the illumination beam is formed.

The radiation source may be monochromatic, in particular a semiconductor laser. A fully chromatic source, in particular white light source, may be used. The radiation beam emitted by the radiation source is by means of the fiber transported without losses to the location of the surface of the sample. Herein, the length of the fiber is optional and can be designed according to the requirements of the measuring head. Because the measuring head has to be as small as possible in order to allow the inspection of curved, in particular concave surfaces, preferably only the illumination beam emitting part of the fiber is arranged inside the measuring head.

In a further preferred embodiment, the radiation source is a flash lamp.

This is advantageous, because the flash lamp is generally included in the camera, used for the imaging of the two dimensional image of the screen. Only one device has to be mounted in the measuring head. This saves space and is cost effective. Preferably the flash is a Xenon flash.

According to a further preferred embodiment, the illumination device comprises a fiber, arranged inside the measuring head in order to direct the illumination beam onto the surface of the sample.

A fiber is a small, longish optical device, which is able to transport the radiation beam nearly loss free.

According to a further preferred embodiment, the fiber is connectable to the radiation source in order to receive the radiation beam and emits the illumination beam.

This allows to position the radiation source outside the measuring head and direct the illumination beam onto the surface of the sample. No further optical components that needs space and are expensive are needed.

According to a further preferred embodiment of the invention, an angle of incidence of the illumination beam at the surface is defined by an optical axis of the fiber, wherein the angle of incidence is smaller than 90° and larger than 0°.

Important in the sense of the invention is only that the illumination component can be put in a close distance to the surface. The radiation source of the illumination device may be positioned outside the measuring head in order to save place.

The surface of the sample may be inspected in reflectance or in transmission. In the latter case, the incident radiation beam and the reflected and/or scattered radiation beam to be detected are at an opposite side of the sample, and the measurement is indicative not only for the physical properties of the entrance and/or exit surface of the sample but also of its interior. The sample can preferably be mounted on an adjustable stage, to allow change in the azimuth of the sample. It is also possible that the sample is in a fixed position and the measuring head is moving, measuring at different positions of the sample.

The fiber allows the direction of the radiation beam very close to the surface, because a fiber has a small diameter, approximately in the range of µ-meters or millimeters. Fibers are also very flexible and easy to handle, if a radiation beam has to be transported in close distance to a location, in particular close to the surface.

Using an angle between 0° and 90° allows the arrangement of the fiber in one quarter of the device and with that a space-saving mounting of the illumination component using only one quarter of the full 360° of the surface of the sample. This leaves space for the mounting of the screen having only the size of a quarter hemisphere. Additionally, space is left for the mounting of additional optical components.

According to a further preferred embodiment of the invention, the angle is smaller than 60° and larger than 5°.

This allows a radiation beam incident on the surface of a sample under an angle between 60° and 5°, wherein the angle is measured between a surface normal and the radiation beam. The illumination component, in particular the fiber, can be mounted closer to the measuring port, resulting in a space-saving arrangement. The illumination component is not shading the reflected and/or scattered radiation beams from the screen. This is advantageous in order to use the whole area of the screen for the detection of the reflected and/or scattered radiation beam, because the screen has a small surface of only a quarter hemisphere.

According to a further preferred embodiment, the angle of incidence is smaller than 45° and larger than 15°.

The ideal angle of the arrangement of the illumination component, in particular the fiber, is about 30°.

According to a further preferred embodiment, the illumination component comprises a collimator assembly allowing the direction of a collimated radiation beam onto the surface of the sample.

With that, small areas of the surface of a sample can be illuminated. Additionally, very small measuring ports can be used.

According to a further preferred embodiment of the invention, the screen is mounted such that a surface normal of the screen and the optical axis of the fiber includes an angle between 80° and 140°, in particular approximately 120°.

With that, the surface normal of the screen and the illumination beam are arranged substantially normal with respect to each other.

Because the distribution of the scattered radiation beam follows substantially a cosinus distribution, this guarantees that a high amount of the scattered and/or reflected intensity of the response beam can be captured by the screen.

According to a further preferred embodiment of the invention, the screen comprises a white coating in order to increase the sensitivity of the screen for the detected response beam.

The screen in a standard optical measurement device comprises a black velvet coating or a Parousiameter gray coating. A flat screen with a Parousiameter gray coating collects about 18% of the reflected radiation beams. With a white coating according to the invention, the sensitivity of the detected radiation beam is increased by the factor of 5. This is important and advantageous because the surface area of the screen is small compared to the full hemispherical screen.

According to a further preferred embodiment of the invention, the measuring head comprises a set of baffles shielding the illumination beam from the screen.

The set of baffles is arranged in the measuring head in order to scrape a beam path to prohibit primary or secondary radiation from other parts of the radiation beam path contaminating the response beam intercepted by the screen. An example for such a baffle is a beam scraper arranged in the optical path of the illumination beam.

According to a further embodiment of the invention, the measuring head comprises a set of baffles, arranged such that the illumination beam is shielded from the image detection component.

An example for a baffle is a screening baffle being arranged perpendicular to an aperture of the camera and/or a beam scraper being arranged perpendicular to the optical axis of the fiber and between the fiber and surface of the sample under a certain angle. The beam scraper is preferably arranged parallel to an opening of the illumination component.

According to a further preferred embodiment of the invention, the measuring head comprises a flat mirror in order to image the screen into the image detection component.

The flat mirror is preferably a folding mirror arranged in front of the aperture of the camera, wherein the angle between the normal of the aperture of the camera and the mirror is approximately 45°.

According to a further preferred embodiment of the invention, the measuring head comprises a casing having a base plate that can be brought into contact with the surface, wherein the base plate comprises a measuring port through which the illumination beam and the response beam are propagating.

The measuring port is positioned at the area of the surface to be inspected and investigated. The measuring port is typically a small opening or view hole through which the illumination beam is propagating to illuminate the surface and as well the response beam is propagating through the measuring port before the response beam is intercepted by the screen.

The size of the measuring port has to be small in order to inspect curved surfaces with a satisfying spatial resolution. The spatial resolution is determined by the number of measuring points in a defined area of the surface. The number of measuring points, which can be arranged in the defined area of the surface, are determined by the size of the measuring port, because the measuring port defines a maximum size of a measuring spot, which is the size of the illumination beam incident on the surface.

According to a further preferred embodiment, the measuring head comprising a top plate, which is connectable with the base plate, wherein the base plate covers a smaller area than the top plate, resulting in a small measuring head.

The measuring head has to be small in size in order to fit into a curved surface during the measurement. This is because the measuring head, in particular the plate or the base plate of the measuring had has to be in close contact with the surface to be investigated.

Preferably, the measuring head has a substantially trapezoidal and/or triangular shape in at least one section plane perpendicular to the surface of the sample.

A shape of the measuring head, seen in a cross-section plane perpendicular to the surface allows that the base plate is smaller than the top plate, the base plate and the top plate are connected by side walls, realizing the trapezoidal or triangular shape. This is the simplest shape of the measuring head and easy to realize.

According to a further embodiment of the invention, the base plate and the top plate are connected by a number of side plates such that the trapezoidal shape of the measuring head is realized.

Preferably, each side of the measuring head comprises two side plates. The trapezoidal shape of the measuring head has the advantage that the inside space of the measuring head is maximized in order to arrange the fiber, the screen and the camera inside the measuring head.

According to a further preferred embodiment of the invention, the measuring head comprises a collimating lens focusing the response beam reflected from the surface of the sample onto the screen in order to obtain a small spot if the surface has mirror properties.

If the surface of the sample has mirror properties, all light is reflected and no or very little scattering takes place. This results in a very bright reflection of the radiation beam, wherein the size of the reflected radiation beam is of the same size as the spot of the illumination component, in particular of the fiber. In order to avoid an overexposure of the screen, the total reflected intensity of the radiation beam is then collimated to a small bright spot being the image of the fiber.

The foregoing and furthermore specific objects and advantages of the present invention will become readily apparent for those skilled in the art, following detailed description of preferred embodiments thereof, taken in conjunction with the drawings, in which.

Figure 1:
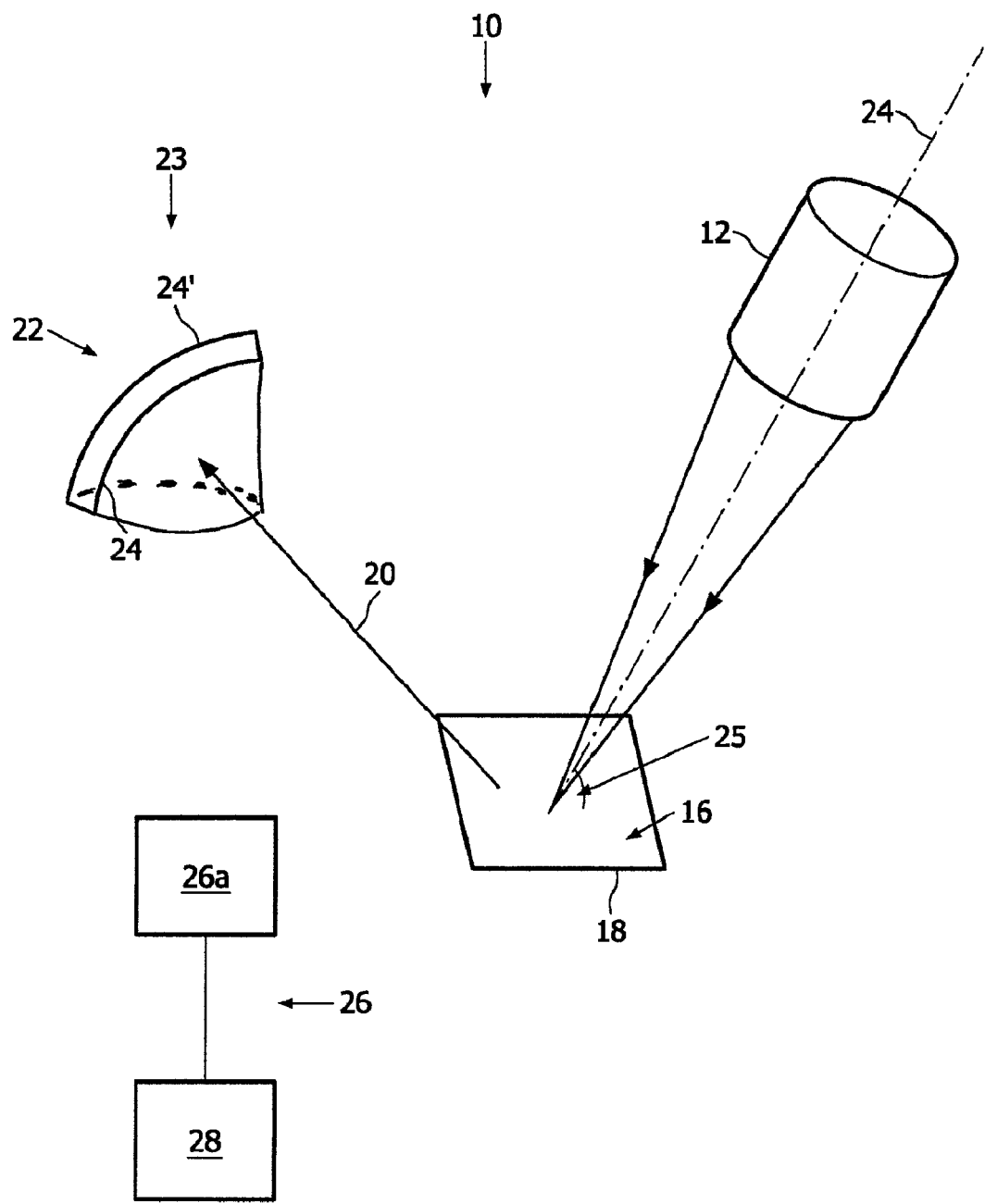
FIG. 1 shows a schematic view of the underlying measuring principle of an optical measurement device for an inspection of a surface of a sample.

In FIG. 1, a schematic view of the measuring principle of an optical measurement device 10 (called Parousiameter) is shown. The optical measurement device 10 is suitable for inspecting a surface of a sample, wherein as a result of the measurement, an optical appearance of the surface, is obtained.

An optical measurement device using the measurement principle is known as Parousiameter. The two-dimensional image is known as Parousiagram. The word "Parousiameter" is deduced from the Greek word "parousia" for optical appearance.

The measuring principle of the optical measurement device 10 is explained in the following.

The optical measurement device 10 comprises an illumination device 12 directing an illumination beam 14 onto a surface 16 of a sample 18. The illumination beam 14 is scattered and/or reflected at the sample, resulting in a response beam 20, wherein the scattered and/or reflected response beam 20 is intercepted by a screen 22.

The illumination device has an optical axis 21, wherein the optical axis 21 defines an angle of incidence 25 of the illumination beam 14 and the surface 16.

This results in that the illumination beam 14 is incident on the surface 16 of the sample 18 under a well-defined direction, the angle of incidence 25. An intensity distribution of the response beam 20 scattered and/or reflected by the surface 16 of the sample 18, is following substantially a cosine distribution. Therefore, the detection component 22 is—in most embodiments—covering the whole hemisphere of 360° above the sample 18. The screen 22 has an inner side 24 and an outer side 24', wherein a diffuse coating is applied to the inner side 24, in order to intercept the intensity distribution of the response beam 20.

A two-dimensional image formed by the response beam 20 on the inner side 24 of the screen 22 is a Fourier-like transform of the optical appearance of the surface 16 of the sample 18. The image is captured by a radiation-sensitive detector, called image detection component 23, which is in particular a camera 26a. The position of the camera 26a shown in FIG. 1 is not representative for the optical measurement device 10, it is just included at an arbitrary position in FIG. 1 to indicate that a camera 26a is used to image the intensity distribution of the second radiation beam from the screen 22.

In some embodiments of optical measurement devices 10, a wide-angle optical system (not shown here) is mounted in front of the camera 26a. The camera 26a provides an electric signal indicated with reference numeral 26, representing the captured image. Calculating component 28 processes the electric signal to derive one or more figures of merit, characterizing the optical appearance of the surface 16 of the sample 18. Herein, a correction factor, called figure of merit, also known as merit function, is a function that measures the agreement between data and a fitting model for a particular choice of parameters. By convention, the figure of merit is small when the agreement is good.

Figure 2:
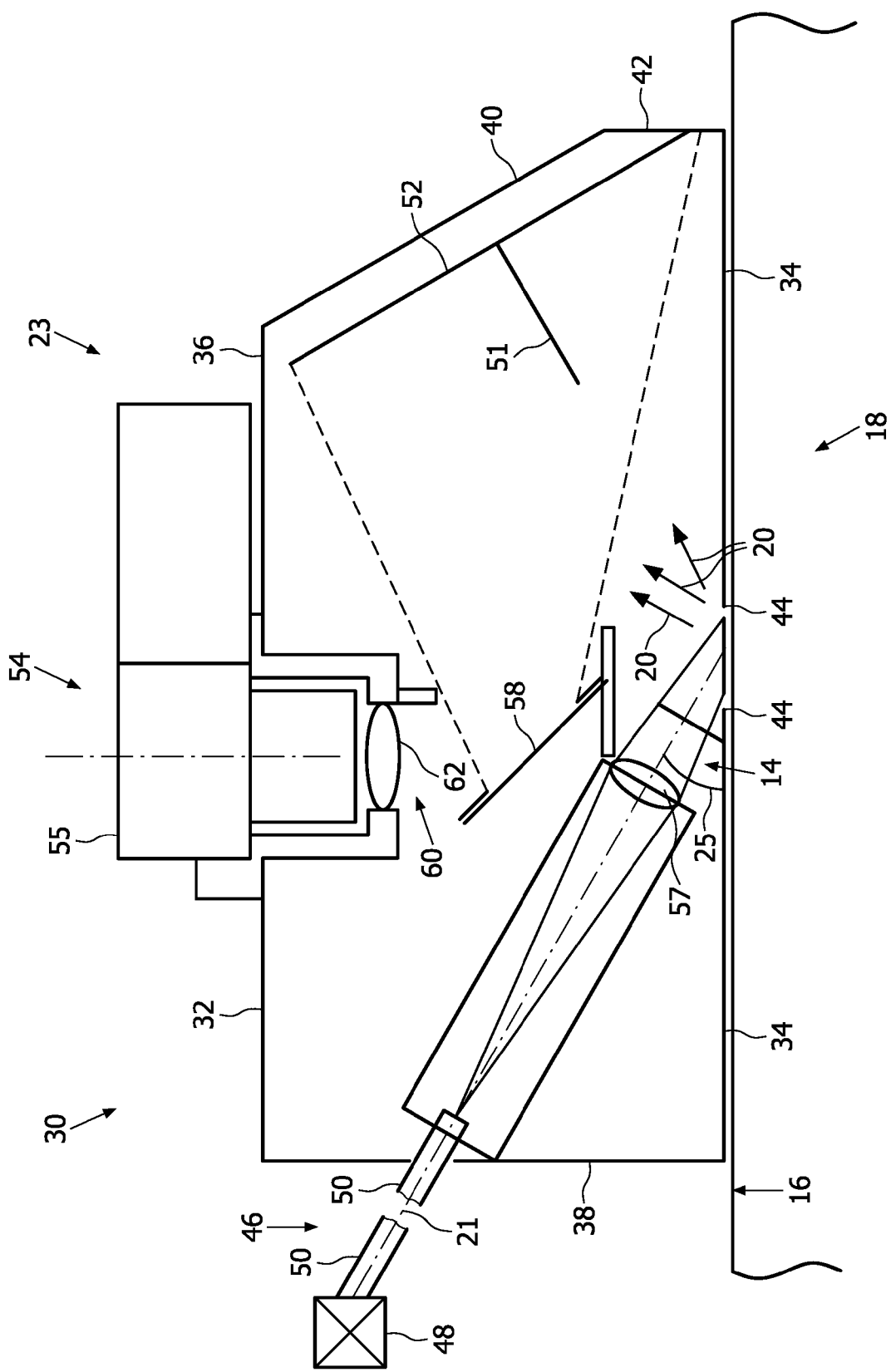
FIG. 2 shows a schematic, cross-sectional view of a measuring head of the optical measurement device in one sectional plane.

FIG. 2 shows a cross-sectional view of a measuring head 30 of the optical measurement device 10, wherein the measuring head 30 is suitable to inspect a surface 16, which is negatively curved, in particular having a concave curvature.

Equal parts are referenced with equal reference numerals as in FIG. 1.

The measuring head 30 comprises a casing 32, wherein the casing 32 comprises a base plate 34 and a top plate 36, a first side plate 38 as well as side plates 40 and 42. Herein, in the embodiment shown in the cross-sectional view, the side plate 38 is arranged opposite to the side plates 40 and 42. The side plate 38 connects the base plate 34 and the top plate 36, wherein at the opposite side the two side plates 40 and 42 are used to perform the connection between top plate 36 and base plate 34. This results in a minimized size of the casing 32 of the measuring head 30.

Figure 3:
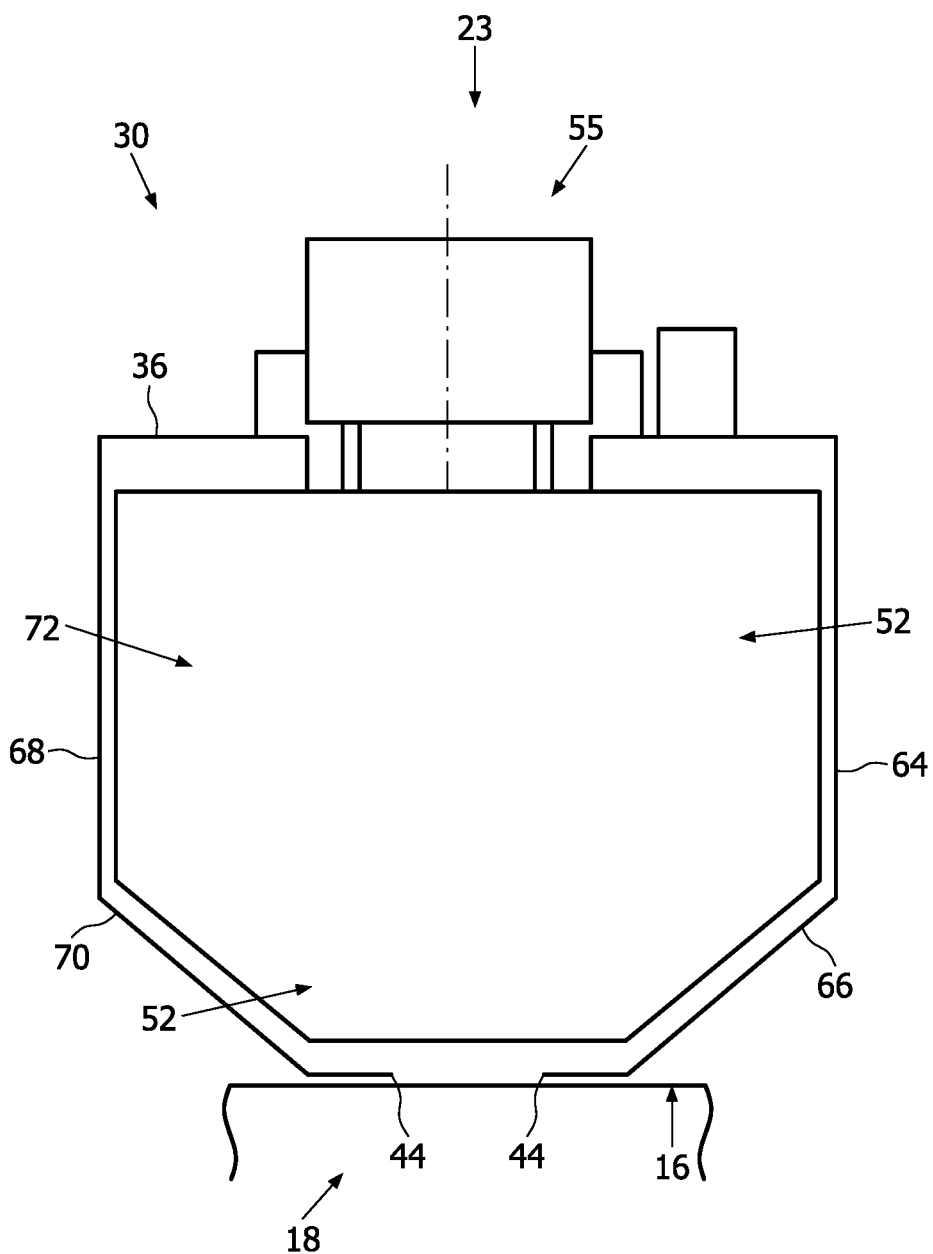
FIG. 3 shows a schematic, cross-sectional view in a sectional plane, perpendicular to the sectional plane of FIG. 2, of the optical measurement device.

A cross-sectional view of the casing 32 in a direction perpendicular to the one shown in FIG. 2 is given in FIG. 3.

The dimension of the base plate 34 is approximately 200 mm in the sectional plane parallel to the surface 16, as shown in FIG. 2.

The base plate 34 comprises a through hole, called measuring port 44. The measuring head 30 further comprises an illumination device 46 comprising a radiation source 48 and a fiber 50, in order to direct the illumination beam 14 through the measuring port 44 onto the surface 16 of the sample 18 to be inspected. The measuring head 30 further comprises a substantially flat screen 52, which intercepts the response beam 20 indicated with three arrows in FIG. 2. The screen 52 has a surface, wherein a surface normal 51 is indicating the direction perpendicular to the surface of the screen 52.

The screen 52 is preferably arranged in the measuring head such that the surface normal 51 includes an angle between 80 and 140° with an optical axis 21 of the fiber 50. The screen 52 is centered with that on the nominal reflection angle.

The measuring head 30 comprises a radiation sensitive image detector, called image detection component 54 arranged in the top plate 36, wherein the image detection component 54 is in particular a camera 26a, preferably a digital camera 55, a CCD camera and the like.

It is to be understood that the radiation source 48 can be a suitable radiation source, in particular a semiconductor laser or a lamp emitting white light or the Xenon flash of the camera 26a or the digital camera 55. The radiation source 48 can be a Xenon flash of the camera 26a or the digital camera 55, if included, wherein the radiation source 48 is attached by a fiber 50.

The space that is gained by using the flat screen 52 extending approximately a quarter hemisphere is used to position the fiber 50 close to the surface 16.

The measuring head 30 further comprises baffles in form of beam scraping elements, wherein a first baffle 57 is arranged between the illumination component 46 and the measuring port 44 and a second baffle 58 is arranged between the screen 52 and an aperture and the digital camera 55. In front of the camera 26a or the digital camera 55, an aperture 60 is arranged in order to limit the radiation incident on the camera 26a or 55.

According to the invention, the flat screen 52 is extending approximately a quarter hemisphere, centered on a nominal reflection angle of the response beam. This saves space and allows the arrangement of the illumination device 46 close to the measuring port 44 of the measuring head 30. The illumination device 46 comprises an optical compound, preferably a lens, in order to form a collimated illumination beam 14. The screen 52 is preferably coated with a white coating, which increases the sensitivity by a factor of five.

The screen 52 is preferably flat, but can also be slightly curved.

The shape of the measuring head 30 is preferably a triangular or trapezoidal shape such that it can fit in a hollow part of the sample, comprising a concave curved surface. The simplest way of connecting a smaller base plate 34 compared to a slightly larger top plate 36 would be a triangular shape. This has the disadvantage that the space inside the measuring head is limited. In order to optimize the space inside the measuring head, a trapezoidal shape in at least one sectional plane perpendicular to the surface, is preferred.

With the measuring head 30 with a small extension, enabled by using the flat screen 52 covering only a quarter hemisphere, especially parts of the human skin can be inspected and the optical appearance of the surface of the skin can be obtained.

The camera 55 comprises a flat mirror 58 that envisages the screen 52 in the camera 55. Because the screen 52 extends approximately a quarter hemisphere, the positioning of the flat mirror, which is a folded mirror, can be arranged inside the small measuring head 30. In front of the camera 55, a lens 62 is preferably mounted with a focal length equal to the distance to the screen 52, which results in that the camera 26a or 55 can be adjusted to infinity. This allows the use of a commercially available digital camera 55 or a CCD camera or a video camera that is capable of acquiring a rapid succession of images to resolve rapid changes in time.

The arrangement of a set of baffles that scrape a beam path separates the illumination beam 14 and the image detection component 54, as well as the illumination beam 14 and the screen 52 to avoid contamination of the measurement by primary or secondary radiation from other parts of the path of the response beam or illumination beam.

The measuring port 44, should be just wide enough to allow the illumination beam 14 to pass through. The measuring head 30 should be applied without pressure onto the surface 10 of the sample 18. In particular, it should be applied without pressure onto the surface 16 of the skin, to avoid to bulk inward and lose its blood perfusion. Preferably relatively flat sections of skin should be selected for measurement of reflections such as parts of the back, abdomen, limbs, forehead or cheek. No major skin plies, wrinkles or folds should be present in the measuring spot, as they are present in many places of the body. On the other side, the measuring head 30 should be applied firm enough to make the skin lie flat against the measuring port 44.

Not shown here, but included in the invention is that the image captured by the camera 55 is processed by an intelligent software that is capable of processing specifically developed image for the extraction of the relevant data, in particular the figure of merit.

FIG. 3 shows a cross-sectional view of the measuring head 30 in a sectional plane perpendicular to the one shown in FIG. 2. The measuring head 30 has a trapezoidal shape as obviously seen in FIG. 3. It can be seen that the casing 32 comprises the top plate 36, the base plate 34 with the view hole, being the measuring port 44, the end side plates 64 and 66, as well as 68 and 70.

Same parts are designated with the same reference numerals as in FIGS. 1 and 2.

Herein, the side plates 64 and 66, as well as the side plates 68 and 70, are performing the connection of the top plate 36 and the base plate 34. The side plate 66 is arranged under an angle larger than 90° relative to the base plate 34 and to the side plate 64. In the same manner, the side plate 70 is arranged under an angle larger than 90° relative to the base plate 34 and the side plate 38. This results in a trapezoidal shape of the casing 32, in order to minimize the shape of the measuring head and maximize the space inside the measuring head the base plate 34 a small dimension. This allows the measuring head 30 to be positioned onto the surfaces 16 of the sample 18 having a concave curvature.

The realization of the measuring head 30 with a small shape can be enabled also by using a different number of side plates in order to connect the base plate 34 and the top plate 36. Also an edgeless shape with rounded edges between the side plates is included in the outline of the invention.

Essentially for the invention is, that the base plate 34 has a smaller area in contact with the surface than the top plate 36.

With arrow 72 the mirror 58, in particular the folding mirror, which is mounted in front of the camera 26a or 55, is indicated.

In a preferred embodiment, the extension of the base plate 34 of the measuring head 30 amounts to approximately 60 mm. The small extension of the base plate 34 and the trapezoidal shape of the casing of the measuring head 30, guarantee that the measuring head 30 can be attached to a surface with a concave curved surface. In particular, a hollow part of a skin of a human being can be inspected according to the optical appearance of the skin by the optical measuring device 10 having the measuring head 30.

The described embodiment of the measuring head 30 of a Parousiameter allows the measurement of the optical appearance of surfaces with negative curvature in one direction. With that, most parts of the human body can be accessed by the Parousiameter according to the invention, having a measuring head 30 as described in FIGS. 2 and 3.

With that, the optical appearance of the skin can be inspected by measuring the radiation distribution reflected and/or scattered at the surface of the skin, wherein the optical appearance is influenced by various factors, including pathology and beautification. In general, human skin has glossy and near-glossy reflection with very specific unisotropies that carry information of deeper layers.

Therefore, using the measuring head 30, having a small base plate 34 and preferably a trapezoidal shape, allows the inspection of the human skin and deducing from the measured optical appearance, to estimate the pathology influencing the skin.

The invention claimed is:

1. An optical measurement device for measuring an optical appearance of a surface of a sample located in a first plane, the optical measurement device comprising a measuring head which can be brought into contact with the surface, the measuring head comprising:
   an illumination device for illuminating the surface with an illumination beam;
   a detection device for detecting a response beam, wherein the response beam is a response to the illumination of the sample with the illumination beam;
   wherein the detection device comprises a screen for intercepting the response beam and an image detection component for imaging the screen, wherein the screen has only a shape of a quarter hemisphere, wherein the illumination device comprises a fiber arranged inside the measuring head in order to direct the illumination beam onto the surface of the sample, wherein the measuring head comprises a flat mirror located in a second plane which is tilted relative the first plane, and wherein the flat mirror is located between theسample and the image detection component for reflecting an image of the screen into the image detection component.

2. The optical measurement device of claim 1, wherein the image detection component comprises a camera.

3. The optical measurement device of claim 1, wherein the illumination device comprises a radiation source emitting a radiation beam from which the illumination beam is formed.

4. The optical measurement device of claim 3, wherein the radiation source comprises a flash lamp.

5. The optical measurement device of claim 1, the fiber is connectable with the radiation source in order to receive the radiation beam and emits the illumination beam.

6. The optical measurement device of claim 1, wherein an angle of incidence of the illumination beam at the surface is defined by an optical axis of the fiber, wherein the angle of incidence is smaller than 90° and larger than 0°.

7. The optical measurement device of claim 6, wherein the angle of incidence is smaller than 60° and larger than 5°.

8. The optical measurement device of claim 6, wherein the angle of incidence is smaller than 45° and larger than 15°.

9. The optical measurement device of claim 1, wherein the illumination device further comprises a collimator assembly that provides a collimated illumination beam onto the surface.

10. The optical measurement device of claim 1, wherein the screen is mounted such that a surface-normal of the screen and the optical axis of the fiber includes an angle between 80° to 140°.

11. The optical measurement device of claim 1, wherein the screen comprises a white coating in order to increase the sensitivity for the detection of the response beam.

12. The optical measurement device of claim 1, wherein the measuring head comprises a set of baffles in order to shield the illumination beam from the screen.

13. The optical measurement device of claim 11, wherein the measuring head comprises a set of baffles arranged such that the illumination beam is shielded from the image detection component.

14. The optical measurement device of claim 1, wherein the measuring head comprises a base plate that can be brought into contact with the surface, wherein the base plate comprises a measuring port through which the illumination beam and the response beam are propagating, and wherein the flat mirror is located between the measuring port and the image detection component.

15. The optical measurement device of claim 14, wherein the measuring head comprises a top plate, which is connectable with the base plate, wherein the base plate covers a smaller area than the top plate.

16. The optical measuring head of claim 14, wherein the base plate and the top plate are connected by a number of side plates such that a trapezoidal shape of the measuring head is realized.

17. The optical measurement device of claim 1, wherein the measuring head comprises a collimating lens focusing the response beam reflected from the surface of the sample onto the screen in order to obtain a small spot on the screen if the surface has mirror properties.

18. The optical measurement device of claim 1, wherein the screen is mounted such that a surface-normal of the screen and an optical axis of the fiber form an angle of approximately 120°.

* * * * *